US009289232B2

(12) United States Patent
Massengale et al.

(10) Patent No.: US 9,289,232 B2
(45) Date of Patent: Mar. 22, 2016

(54) SOFT TISSUE TUNNELING DEVICE

(75) Inventors: Roger Massengale, Mission Viejo, CA (US); Mark Siminuk, Lake Forest, CA (US); Alan Dine, Pleasant Plain, OH (US); Doug Carroll, Concord, NC (US)

(73) Assignee: Avent, Inc., Alpharetta, GA (US)

( * ) Notice: Subject to any disclaimer, the term of this patent is extended or adjusted under 35 U.S.C. 154(b) by 394 days.

(21) Appl. No.: 11/744,667

(22) Filed: May 4, 2007

(65) Prior Publication Data

US 2008/0086161 A1    Apr. 10, 2008

Related U.S. Application Data

(60) Provisional application No. 60/798,238, filed on May 5, 2006.

(51) Int. Cl.
*A61B 17/00* (2006.01)
*A61B 17/34* (2006.01)
*A61M 25/01* (2006.01)

(52) U.S. Cl.
CPC ........ *A61B 17/3415* (2013.01); *A61M 25/0194* (2013.01); *A61M 2025/0197* (2013.01)

(58) Field of Classification Search
CPC .......... A61B 17/3415; A61B 17/3417; A61M 25/06; A61M 25/0194; A61M 25/0625; A61M 39/1011; A61M 2005/2073; A61M 2005/2451; A61M 2025/0197
USPC .................. 606/190, 191, 193; 604/104–109, 604/164.01, 164.02, 164.05, 164.08, 164.1, 604/39–45, 93.01, 264, 528–532
See application file for complete search history.

(56) References Cited

U.S. PATENT DOCUMENTS 623,022 A *  4/1899  Johnson ........................ 607/116
722,542 A *  3/1903  Smedley ....................... 604/104
(Continued)

FOREIGN PATENT DOCUMENTS

GB    2377889 A    1/2003
JP    2003062068    3/2003
(Continued)

OTHER PUBLICATIONS www.merriam-webster.com/dictionary/malleable, definition of the term "malleable," retrieved Apr. 8, 2014.*
(Continued)

*Primary Examiner* — David C Eastwood
(74) *Attorney, Agent, or Firm* — Dority & Manning, P.A.

(57) ABSTRACT

A tissue tunneling device is configured to be delivered within the body. The tunneling device includes a shaft with a blunt distal end to prevent coring or other damage to tissue during the delivery of the tunneling device. In some arrangements, the shaft includes one or more lumen, through which medication or another fluid may be administered. An anesthetic or other pain relieving medication may be delivered through the lumen to lessen the discomfort of delivering the tunneling device to the desired anatomical site. The shaft may also include a retractable needle for facilitating the advancement of the tunneling device through skin or other tissue. The shaft may also be provided with an outer sheath, which may be left within the anatomy after the tunneling device has been removed. The shaft may be malleable for custom-shaping the tunneling device prior to and/or during delivery.

18 Claims, 6 Drawing Sheets

(56) References Cited

U.S. PATENT DOCUMENTS

| | | | |
|---|---|---|---|
| 1,957,673 A * | 5/1934 | Sayre | 606/191 |
| 4,191,186 A * | 3/1980 | Keeler | 604/164.07 |
| 4,578,061 A | 3/1986 | Lemelson | |
| 5,141,497 A * | 8/1992 | Erskine | 604/164.05 |
| 5,300,032 A | 4/1994 | Hibbs et al. | |
| 5,306,240 A | 4/1994 | Berry | |
| 5,441,504 A * | 8/1995 | Pohndorf et al. | 606/129 |
| 5,630,802 A | 5/1997 | Moellmann et al. | |
| 5,741,233 A * | 4/1998 | Riddle et al. | 604/165.01 |
| 5,868,729 A | 2/1999 | Pelfrey | |
| 5,885,217 A * | 3/1999 | Gisselberg et al. | 600/434 |
| 6,010,495 A * | 1/2000 | Tilton, Jr. | 606/1 |
| D449,887 S | 10/2001 | Haberland et al. | |
| 6,336,914 B1 | 1/2002 | Gillespie, III | |
| 6,589,262 B1 | 7/2003 | Honebrink et al. | |
| 6,641,564 B1 | 11/2003 | Kraus | |
| 6,645,178 B1 * | 11/2003 | Junker et al. | 604/164.05 |
| 6,663,595 B2 * | 12/2003 | Spohn et al. | 604/161 |
| 6,685,648 B2 | 2/2004 | Flaherty et al. | |
| 7,232,425 B2 | 6/2007 | Sorenson et al. | |
| 8,211,136 B2 * | 7/2012 | Griffith et al. | 606/191 |
| 2002/0107506 A1 | 8/2002 | McGuckin | |
| 2003/0088212 A1 | 5/2003 | Tal | |
| 2003/0216771 A1 * | 11/2003 | Osypka et al. | 606/191 |
| 2004/0116896 A1 * | 6/2004 | Massengale | 604/506 |
| 2004/0204735 A1 * | 10/2004 | Shiroff et al. | 606/190 |
| 2004/0230204 A1 | 11/2004 | Wortley et al. | |
| 2004/0236313 A1 * | 11/2004 | Klein | 604/537 |
| 2005/0113768 A1 | 5/2005 | Patrickson | |
| 2005/0119619 A1 | 6/2005 | Haining | |
| 2005/0131392 A1 * | 6/2005 | Chu et al. | 606/1 |
| 2005/0253390 A1 * | 11/2005 | Blazek | A61M 39/1011 285/420 |
| 2005/0261718 A1 * | 11/2005 | Petros et al. | 606/190 |
| 2006/0122676 A1 * | 6/2006 | Ko et al. | 607/116 |
| 2006/0149293 A1 * | 7/2006 | King et al. | 606/108 |
| 2006/0200079 A1 * | 9/2006 | Magnusson | 604/164.1 |

FOREIGN PATENT DOCUMENTS

| | | |
|---|---|---|
| WO | WO 2006/050191 | 5/2006 |
| WO | WO 2007/114875 | 10/2007 |

OTHER PUBLICATIONS

International Search Report for Application No. PCT/US2007/010890 mailed Oct. 22, 2007.

* cited by examiner

SOFT TISSUE TUNNELING DEVICE

RELATED APPLICATION

This application is related to, and claims the benefit of, U.S. Provisional Patent Application No. 60/798,238, filed May 5, 2006, the entirety of which is hereby incorporated by reference herein and made a part of the present disclosure.

BACKGROUND OF THE INVENTION

1. Field of the Invention

This invention generally relates to soft tissue tunneling devices and, in particular, to an improved tunneling device for the introduction of a catheter into the body of a patient.

2. Description of the Related Art

Devices used to administer a fluid inside the anatomy are well known. Hypodermic needles, catheters and the like are often used to deliver medication and other fluids to targeted sites within the body. In many instances, catheters are preferred because they can deliver fluid to a particular site over a period of time. However, catheters often require stiff, hollow introducer needles for placement within the anatomy. Typically, such introducer needles have sharp tips that may damage tissue and/or nerves during their delivery into a body. This trauma may also result cause discomfort for the patient.

SUMMARY OF THE INVENTION

A need exists for an improved tunneling device with a blunt distal tip to minimize coring of tissue and other damage associated with advancing an object within the body. The tunneling device may optionally include a retractable needle to assist in puncturing the skin prior to advancing the tunneling device within the patient's body. In addition, a tunneling device with a shapeable malleable shaft will assist in the accurate delivery of the device into the anatomy. Moreover, a tunneling device configured to deliver anesthetic or other medication to the tissue adjacent to the tissue adjacent the tunneling device will alleviate the discomfort associated with such procedures.

A preferred embodiment involves a tunneling device for creating a subcutaneous path for placement of a catheter in a patient. The tunneling device includes an elongate shaft having a rounded distal end. A handle is secured to the shaft. The handle is configured to permit a user of the tunneling device to manually manipulate the tunneling device.

A preferred embodiment involves a tunneling device for creating a subcutaneous path for placement of a catheter in a patient. The tunneling device includes an elongate shaft having a rounded distal end. A handle is secured to the shaft. The handle is configured to permit a user of the tunneling device to manually manipulate the tunneling device. A sheath is positionable over a portion of the shaft. The sheath has a snug fit with the shaft such that the sheath and the shaft can be advanced together within a body of a patient.

A preferred embodiment involves a tunneling device for creating a subcutaneous path for placement of a catheter in a patient. The tunneling device includes an elongate shaft. The shaft has a rounded distal end and defines an interior lumen. A handle is secured to the shaft. The handle is configured to permit a user of the device to manually manipulate the device. At least one fluid exit opening is positioned along the length of the shaft and extends from the interior lumen to an external surface of the shaft. An inlet to the interior lumen to permits liquid to be introduced into the interior lumen and administered to the patient through the at least one fluid exit opening.

A preferred method of introducing a tunneling device into a body involves grasping a handle of a tunneling device, the tunneling device comprising an elongate shaft having a rounded distal end and defining at least one interior lumen and at least one fluid exit opening in fluid communication with the interior lumen. The method also includes introducing the tunneling device into the body of a patient and advancing the tunneling device within the body. Fluid is administered through the interior lumen and into the body of the patient.

A preferred embodiment involves a tunneling device for creating a subcutaneous path for placement of a catheter in a patient. The tunneling device includes an elongate shaft having a rounded distal end. A handle is secured to the shaft and is configured to permit a user of the tunneling device to manually manipulate the tunneling device. The shaft is malleable so as to permit a shape of the shaft to be altered prior to use of the tunneling device.

A preferred embodiment involves a tunneling device for creating a subcutaneous path for placement of a catheter in a patient. The tunneling device includes an elongate shaft having a rounded distal end. A handle is secured to the shaft and is configured to permit a user of the tunneling device to manually manipulate the tunneling device. The shaft is preshaped to have a non-linear shape.

BRIEF DESCRIPTION OF THE DRAWINGS

These and other features, aspects and advantages of the present soft tissue tunneling device are described in detail below with reference to drawings of certain preferred embodiments, which are intended to illustrate, but not to limit, the present inventions. The drawings contain six (6) figures. It is to be understood that the attached drawings are for the purpose of illustrating concepts of the present inventions and may not be to scale.

DETAILED DESCRIPTION OF THE PREFERRED EMBODIMENTS

Figure 1A:
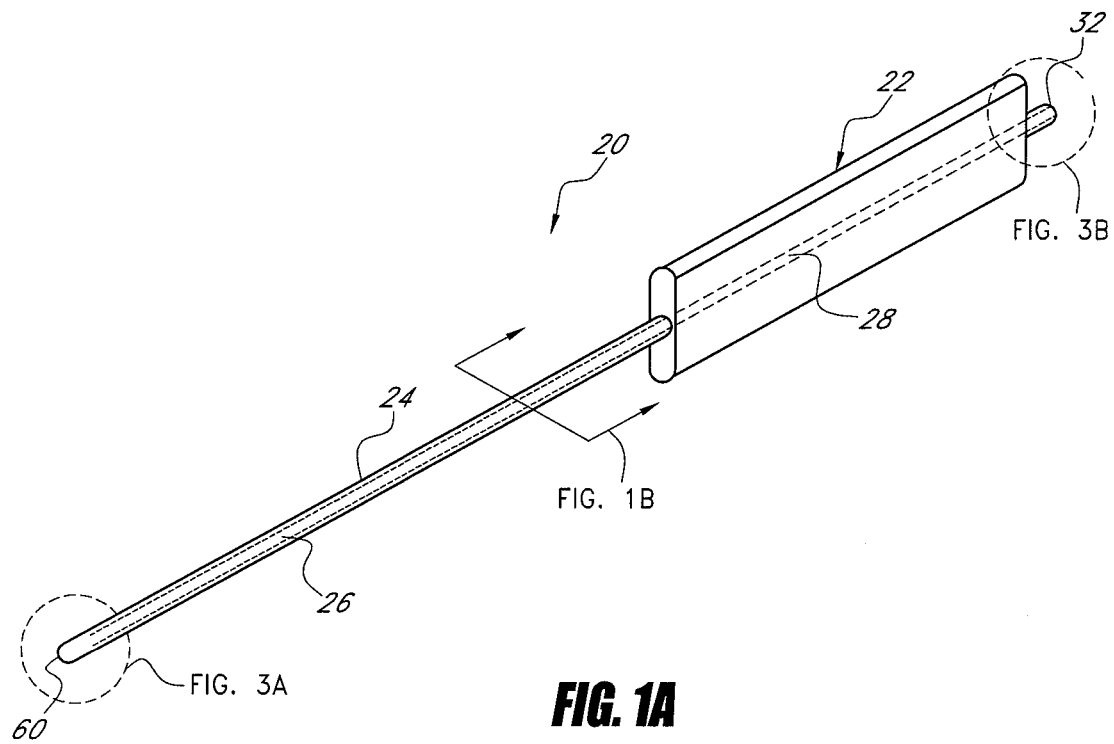
FIG. 1A is a perspective view of a tunneling device having certain features, aspects and advantages of the present invention.

FIG. 1A illustrates a soft tissue tunneling device 20 according to one embodiment of the present invention. The tunneling device 20 preferably includes a handle 22, a shaft 24 and at least one lumen 26 located within the shaft 24. The handle 22 can be constructed of one or more types of plastic or other synthetic or semi-synthetic polymerization product. Alternatively, the handle 22 may be constructed of metal and/or any other suitable material or combination of materials. As illustrated in FIG. 1A, the handle 22 has a generally rectangular shape in cross-section with rounded edges. Preferably, the handle 22 is easy to grip to assist the user in grasping and manipulating the tunneling device 20. The handle 22 can be manufactured with smooth corners and/or other surfaces to reduce any discomfort of handling the tunneling device 20. Further, the handle may have a plurality of molded finger grooves or the like for enhanced gripability. Moreover, a portion or the entire handle 22 may be provided with a non-slip surface. For example, the surface of the handle 22 may textured or covered with a rubber material.

In one embodiment, the handle 22 is approximately 4 inches long by 1 inch wide by 3/8 inch thick. However, those of skill in the art will appreciate that the length, width and/or thickness of the handle 22 may be greater or lesser than indicated above. In addition, the handle 22 may include one or more knobs, levers, buttons or other control devices to operate any functional aspect of the tunneling device 20 (e.g., retractable needle). As described in greater detail below, the handle 22 can preferably include an interior passageway 28. In some embodiments, the interior passageway 28 is in fluid communication with a luer fitting 32 or other type of connection.

The shaft 24 preferably is constructed of a polymeric material, stainless steel or a combination of both. However, those of skill in the art will appreciate that the handle 22 and the shaft 24 may be constructed of any other suitable material. Further, the shaft 24 of the tunneling device 20 may be configured without a lumen 26.

Figure 3A:
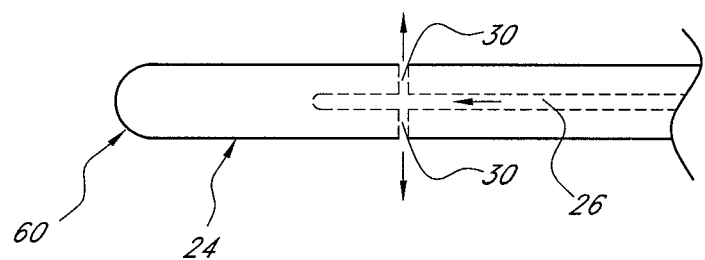
FIG. 3A is a view of a distal end portion of the tunneling device of FIG. 1A with certain features shown in phantom.

In the depicted embodiment, the lumen 26 extends to the distal end of the shaft 24. With reference to the cross-sectional detail in FIG. 3A, the lumen 26 includes at least one, and preferably two outlets 30 that extend to the outside of the shaft 24. The outlets 30 are located near the distal end of the shaft 24 and are oriented opposite of one another (180 degrees apart). However, it will be recognized that the exact number and location of outlets 30 along the length of the shaft 24 may vary. For example, a plurality of openings 30 may be positioned along the entire length of the lumen 26. Alternatively, openings 30 may be situated along one or more portions of the shaft 24 (e.g., the distal end, the middle portion and/or the proximal end). In FIG. 3A, like the lumen 26 to which they are hydraulically connected, the openings 30 preferably have a circular cross-section for more efficient fluid flow. However, the cross-section of the lumen 26 and/or the openings 30 may have any suitable shape. For example, the openings 30 may have a rectangular cross-section with the long end of the opening 30 parallel to the longitudinal end of the shaft 24.

Figure 1B:
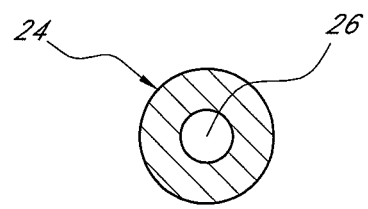
FIG. 1B is a cross-sectional view of the shaft of the tunneling device of FIG. 1A taken along the line labeled FIG. 1B in FIG. 1A.

With continued reference to FIG. 3A, the lumen 26 extends a short distance beyond (more distal to) the location of the outlets 30. In other embodiments, the lumen 26 may extend even further towards the distal tip of the shaft 24. Alternatively, the lumen 26 may only extend as far as the most distally located outlet 30. In the embodiment depicted in FIG. 1A, the diameter of both the shaft 24 and the lumen 26 remain constant for the entire length of the tunneling device 20. However, the cross sectional shape of the shaft 24 and/or the one or more lumen 26 situated within the shaft 24 may vary along the length of the shaft 24. In one embodiment, the cross-sectional area of the shaft 24 and/or the lumen 26 may decrease with increasing distance from the handle 22. Further, as shown in FIG. 1B, the lumen 26 is concentric to the shaft 24. In other embodiments, the orientation of the lumen 26 within the shaft 24 may be different, especially if the shaft 24 includes two or more lumens 26.

In one embodiment, the shaft 24 is approximately 8 inches long and has an outside diameter of approximately one-eighth of an inch. In another preferred arrangement, the shaft 24 has a diameter of about 0.118 inches. Of course, those of skill in the art recognize that the shaft may be shorter or longer and its diameter may be smaller or larger to satisfy a particular application.

The lumen 26 is preferably in fluid communication with a passageway 28 provided in the handle 22. The combination of the lumen 26 and passageway 28 may be referred to herein generally as a "lumen." In FIG. 1B, the passageway 28 within the handle 22 extends to the proximal end of the handle 22. More preferably, as detailed in FIG. 3B, a luer fitting 32 or other connection device is included at the proximal end of the handle 22. Thus, a fluid delivery device, such as a syringe, a drug delivery pump or the like, may be connected to the luer fitting 32 for the administration of a fluid through the passageway 28, and consequently, to the downstream lumen 26. In an alternative arrangement, a fluid delivery device may be integrated with the tunneling device 20. For example, a fluid delivery device may be integrated with the handle 22 and may provide a mechanism for pressurizing the fluid. The passageway 28 may alternatively terminate on any other suitable portion of the handle 22 (e.g., side surface, proximal end, etc.). In embodiments where the handle 22 is not configured with an inner passageway 28, the lumen 26 exit hole, a luer fitting 32 or other suitable connection device may be included directly on the shaft 24.

Figure 2A:
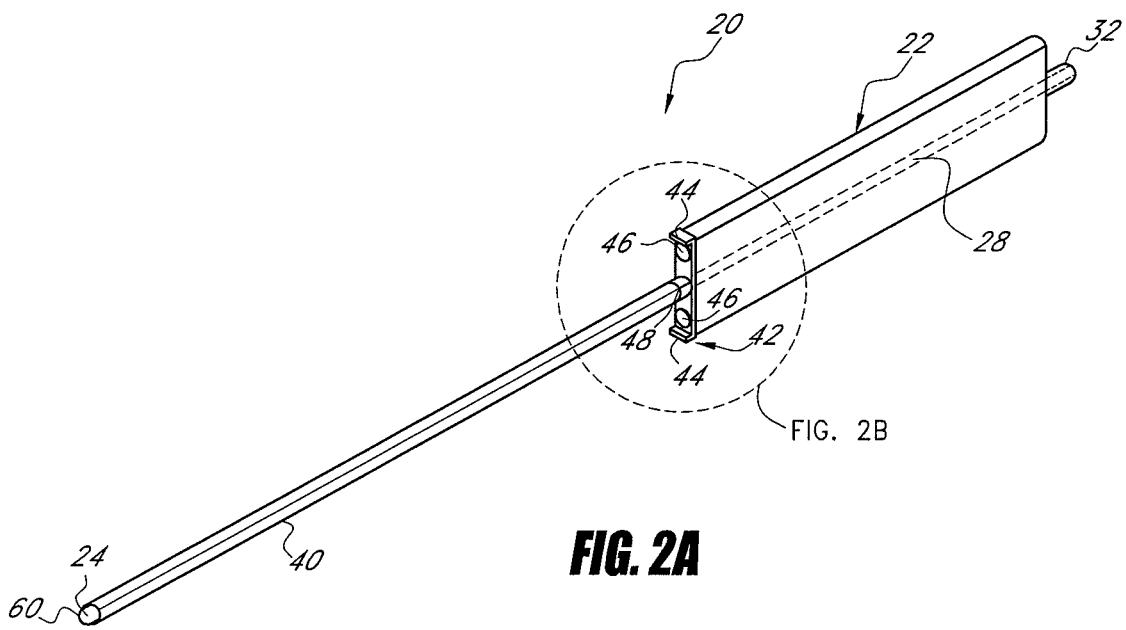
FIG. 2A is a perspective view of the tunneling device of FIG. 1A with a sheath covering a portion of the shaft.

In FIG. 2A, the tunneling device 20 further includes a sheath 40 around the shaft 24. The sheath 40 is preferably manufactured from polyethylene or some other flexible material. However, the sheath 40 may be formed from any of a variety of suitable materials giving due consideration to the goals of flexibility, weight, strength, smoothness, safety, non-reactivity to anatomical systems, etc. Preferably, the inside diameter of the sheath 40 is slightly larger than the outside diameter of the shaft 24, allowing the sheath 40 to fairly easily, but snugly slide over the outer surface of the shaft 24. Preferably, the fit between the shaft 24 and the sheath 40 is such that the pair may be advanced within the body without tissue entering between the shaft 24 and the sheath 40. In some arrangements, the shaft 24 may include a recessed portion to receive the sheath 40. The sheath 40 is configured to cover a substantial majority of the length the shaft 24. In addition, the length of the sheath 40 is preferably selected so as to not cover the one or more outlets 30 of the shaft 24 when the sheath 40 is in its most proximal position on the shaft 24. Thus, in such embodiments, the distal end of the shaft 24 is not covered by the sheath 40 when the sheath 40 is slid against the handle 22.

Figure 2B:
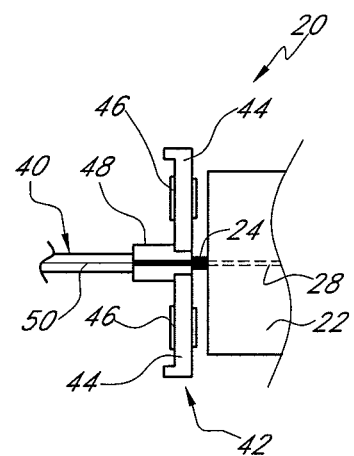
FIG. 2B is a detailed side view of a portion of the tunneling device of FIG. 2A identified by the circle labeled FIG. 2B in FIG. 2A.

In the embodiment illustrated in FIGS. 2A and 2B, the sheath 40 includes a handle portion 42 near its proximal end. The handle portion 42 includes two tabs 44 located opposite of one another. Those of skill in the art will appreciate that the handle portion 42 of the sheath 40 may be configured with more than two tabs 44. As depicted, each tab 44 includes raised contact members 46 on both its distal and proximal sides. The raised contact members 46 may act to restrict the movement of the sheath 40 relative to an adjacent object (e.g., the handle 22, a patient's skin, etc.) and facilitates grasping of the tabs 44. The sheath 40 also includes a hub 48 that connects the tabs 44 to the main distal portion of the sheath 40. As illustrated in FIG. 2B, the sheath 40, including the hub 48, may be configured with a seam 50 along its longitudinal axis.

Preferably, the sheath 40 includes at least two parallel seams 50, one on each side of the sheath 40. In other embodiments, more a sheath 40 may be configured with more than two seams 50. As will be discussed in greater detail below, the seams 50 make it easier for a user to peel apart the sheath 40 after the catheter has been positioned within the anatomy. In the depicted embodiment, a user splits the sheath 40 along the one or more seams 50 by pulling apart the tabs 44 of the handle portion 42. Consequently, this facilitates removal of the sheath 40 when one or more objects are situated within the sheath 40 (e.g., a catheter, an instrument, etc.). The seams 50 preferably extend to the distal end of the sheath 40.

Preferably, the shaft 24 of the tunneling device 20A has a blunt distal end 60, as shown in FIGS. 1A and 2A. The blunt distal end 60 helps minimize or eliminate the coring of tissue as the tunneling device 20 is advanced through the anatomy. Further, the blunt distal end 60 inhibits or eliminates damage to nerves and other sensitive tissues. In the depicted embodiments, the blunt distal end 60 is generally rounded and, more particularly, substantially spherical and is the same diameter as the shaft 24. However, any suitable blunt (non-sharp) shape can be used.

Figure 4A:
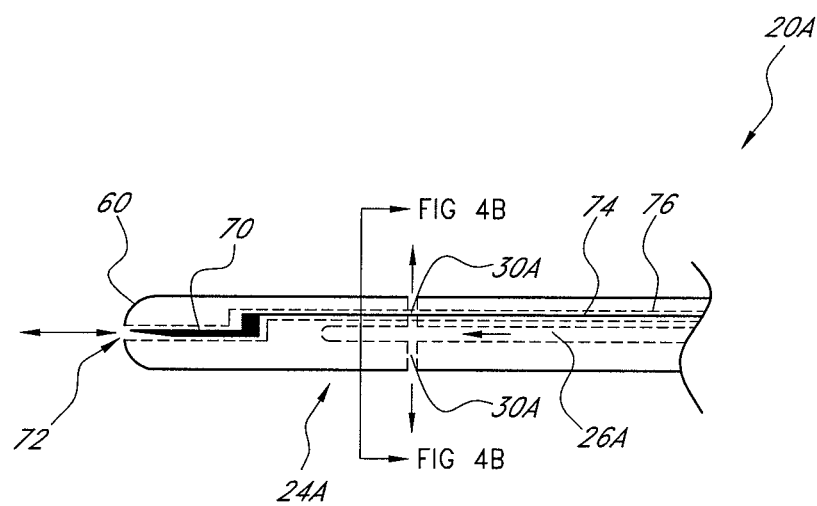
FIG. 4A is a view of a proximal end of a tunneling device according to another embodiment with certain features shown in phantom.
Figure 4B:
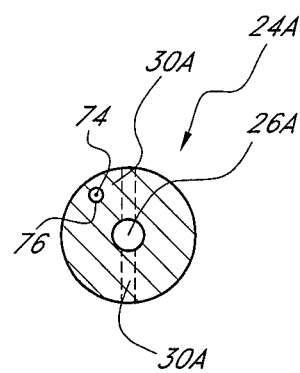
FIG. 4B is a cross-sectional view of the tunneling device of FIG. 4A, taken along the line labeled FIG. 4B in FIG. 4A.

FIG. 4A illustrates a cross-sectional longitudinal view of a shaft 24A according to another embodiment of the tunneling device 20A. The shaft 24A includes a retractable needle 70 that may be used to penetrate the skin, thus, facilitating the introduction of the tunneling device 20 into the anatomy. Preferably, the retractable needle 70 is housed within the distal end of a needle lumen 76, and may be fully retracted within the needle lumen 76 so that the shaft 24A maintains a substantially blunt distal end 60. The position of the retractable needle 70 within the needle lumen 76 may be changed using any suitable method. For example, in FIG. 4A, the position of the needle 70 is controlled by axially moving a rod 74 that is coupled to the needle 70. In other embodiments, a wire or other suitable member may be used in lieu of a rod 74. As depicted, the rod 74 is housed within the needle lumen 76 of the shaft 24A. Preferably, the rod 74 and the corresponding needle lumen 76 extend proximally to the handle 22 of the tunneling device 20A to permit a user to easily control the position of the retractable needle 70 by hand or by using a control member or other device (not shown). Non-limiting examples of suitable control members include knobs, levers, etc. Alternatively, the rod 74 or other suitable member for controlling the position of the retractable needle 70 may be positioned within the fluid delivery lumen 26.

Regardless of how the needle 70 is manipulated between forward and retracted positions, the shaft 24A may optionally include one or more lumens 26A and/or openings 30A hydraulically connected to such lumen 26A. Preferably, the opening 72 through which the tip of the needle 70 can pass is relatively small in comparison to the total cross-sectional area of the blunt distal end 60 so that the surface on the blunt distal end 60 of the shaft 24A is as smooth and continuous as practicable. In other embodiments, the shaft 24A may include a membrane or other suitable covering when the needle 70 is in the retracted position to create a smoother surface on the blunt distal end 60. Further, the opening 72 may have any suitable shape, size and overall orientation. In the embodiment shown in FIG. 4A, the opening 72 is substantially circular and is concentric with the shaft 24A. Moreover, in an alternative arrangement, the needle 70 may be positioned within the lumen 26A through which fluid is also delivered from the tunneling device 20A, as described below.

Preferably, one or more openings 30A hydraulically connected to a lumen 26A of the shaft 24A are located near the retractable needle 70. Such an arrangement allows an anesthetic or other fluid to be delivered near the site of the needle penetration. In one embodiment, the opening 72 for the needle 70 is itself hydraulically connected to the lumen 26A, further facilitating delivery of anesthetic or other fluid to the area proximate the needle 70.

Figure 5:
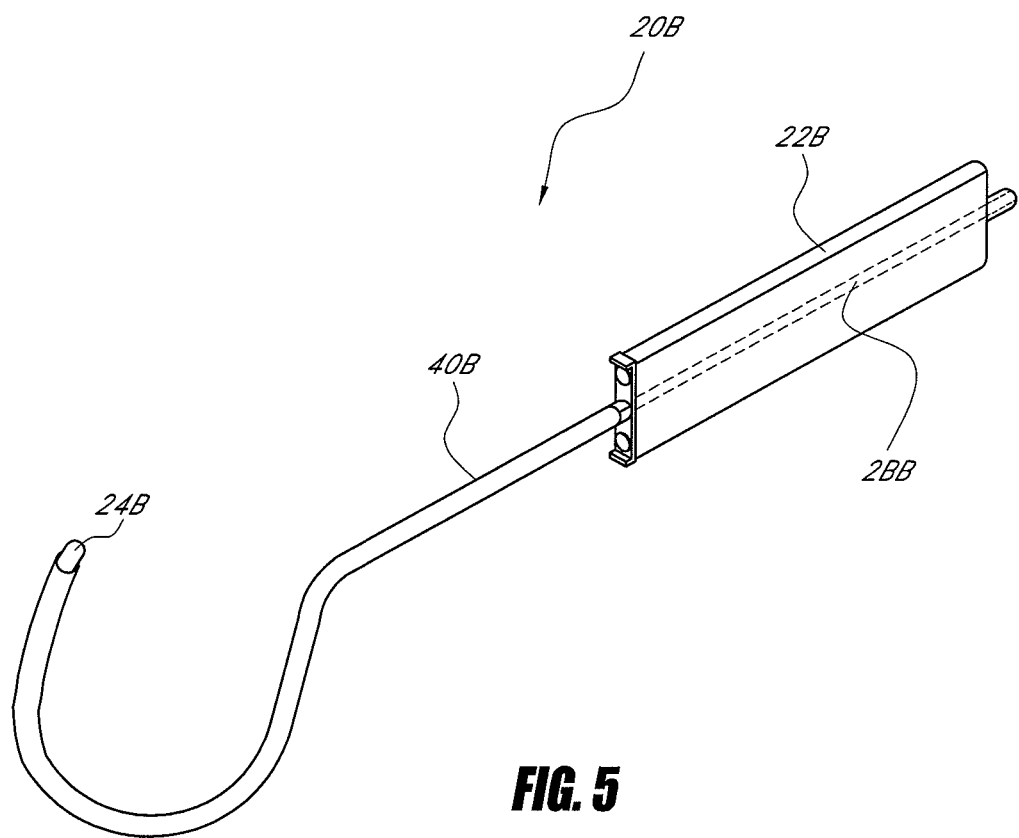
FIG. 5 is a perspective view of a tunneling device according to yet another embodiment.
Figure 6:
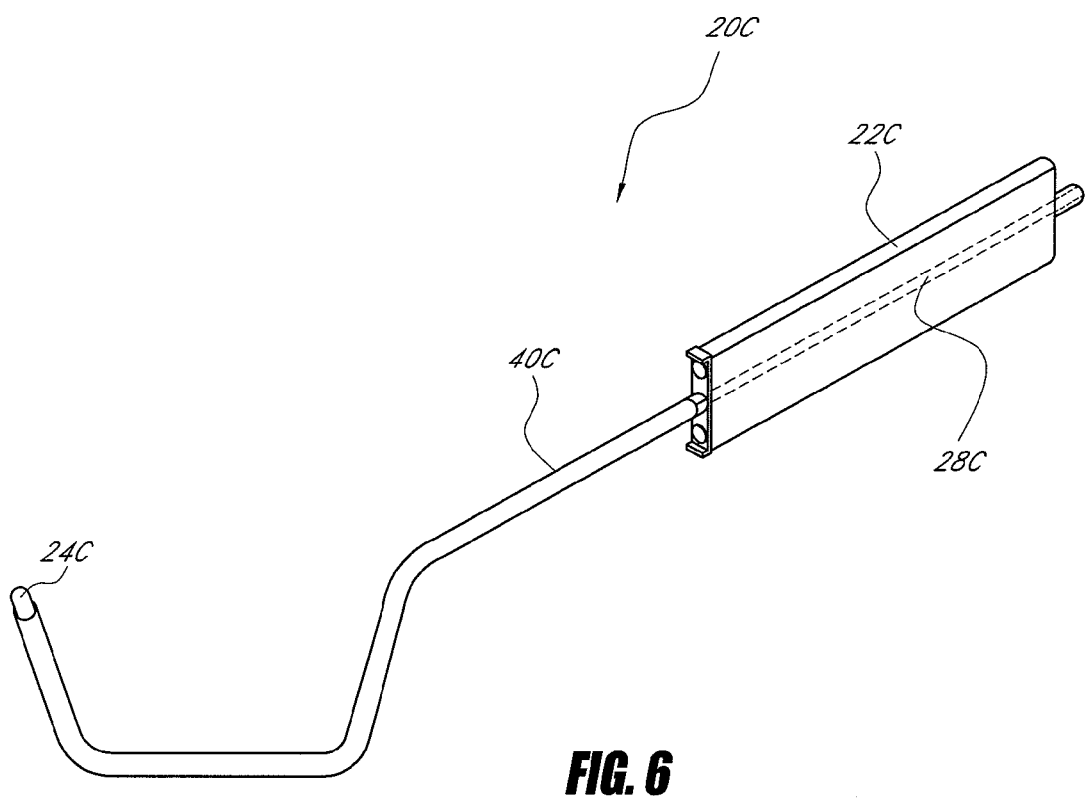
FIG. 6 is a perspective view of a tunneling device according to still another embodiment.

With regard to all the embodiments discussed herein, the shaft of the tunneling device may be manufactured from a malleable material, such as malleable stainless steel. A malleable shaft permits a user to customize the shape of the tunneling device prior to and/or during insertion of the tunneling device into the anatomy. In FIG. 5, the shaft 24B has been bent into a non-linear two-dimensional shape, e.g., a hook shape. The shape of the malleable shaft 24 may be more or less intricate, as may be required by a particular procedure. For example, FIG. 6 depicts a further embodiment of the tunneling device 20C, having a shaft 24C bent into a more convoluted, three-dimensional shape. In such embodiments, the shaft may be formed from a variety of materials, giving due consideration to the goals of malleability, strength, safety and other factors. For example, a stiffer shaft may be desired if a tunneling device is shaped prior to insertion into the anatomy, such as during the manufacturing process. This will better preserve the pre-shaped form of the shaft as the tunneling device is advanced into the anatomy. Alternatively, a more malleable material may be preferred if the shaft will be shaped immediately prior to the delivery of the tunneling device within the anatomy, such as by the user performing the tunneling procedure. Regardless, the tunneling device is preferably configured to prevent the collapse of any interior lumen and any other opening situated inside the shaft. This ensures that the various features of the tunneling device (e.g., fluid delivery through the shaft, the retractable needle, etc.) function properly. For example, if an inner lumen of the shaft collapses or is otherwise obstructed, the administration of fluid to the one or more outlets of the shaft may not be possible.

With continued reference to FIG. 2A, the tunneling device 20 is introduced into the anatomy with the intent to reach a particular location. The tunneling device 20 may be used to aid in the subsequent placement of a catheter or other device. Alternatively, the tunneling device 20 may be used for the direct delivery of a fluid to a targeted site within the anatomy. In use, typically, the tunneling device 20 must first penetrate the skin. In a preferred embodiment, the tunneling device 20 comprises a sharp retractable needle 70 at the distal end of the shaft 24 for piercing the skin (FIG. 4A). Once the skin has been penetrated, the retractable needle 70 is withdrawn into its opening 72, and the shaft 24 of the tunneling device is pushed towards the target area within the anatomy. As depicted in FIG. 4A, the axial position of the needle 70 may be controlled by manipulating a rod 74 that is coupled to the needle 70. Alternatively, a wire or other suitable member may be use in lieu of the rod 74. The rod 74 or other member is situated within lumen 76 of the shaft 24A, and preferably extends to the handle of the tunneling device 20A. The position of the rod 74 or other member (and thus, the position of the needle) may be controlled by hand or by a control member (e.g., knob, lever, etc.) that may be advantageously located on or near the handle. Those of skill in the art will recognize that any other suitable method of controlling the position of the needle 70 can be used. This allows the person using the tunneling device 20A to easily control the position of the needle 74 during all stages of the tunneling procedure.

Once the tunneling device 20 has been inserted under the skin, it is directed, usually between the skin and muscle tissue, to the target region within the body. Preferably, the distal end of the shaft 24 is blunt in order to inhibit damage to sensitive tissues such as nerves. For example, the blunt distal end minimizes coring of tissue as the tunneling device 20 is moved through the anatomy. For example, as illustrated in FIGS. 1A and 2A, the shape of the distal end 60 of the shaft 24 is rounded. After the tunneling device 20 has been inserted under the skin, it may be desirable or necessary to once again penetrate obstructive tissue using the retractable needle 70. Therefore, if the need arises, the needle 70 may be directed distally out of the opening 72 to protrude from the distal end 60 of the shaft 24A. Once the needle 70 has adequately penetrated the target tissue, it may be retracted, permitting the blunt distal end 60 of the shaft 24A to guide the tunneling device 20A through the adjacent anatomical tissue.

Preferably, the shaft 24 includes one or more lumens 26, through which fluid can be administered as the tunneling device 20 is being introduced and delivered to its target site. For example, one or more pain relieving medications, e.g., local anesthetic, may be fed into the lumen 26 to alleviate the pain associated with the tissue tunneling process. In some embodiments, the pain relieving medication or other fluid is delivered to the distal portion of the shaft 24 through one or more outlets 30 (FIG. 3A). Alternatively, as described above, the lumen 26 may be configured with additional outlets 30 positioned at various locations along the length of the shaft 24 to deliver the medication or other fluid to a greater extent of the anatomy. More preferably, the medication or other fluid is intermittently or constantly fed into the lumen to relieve pain throughout the entire tunneling procedure.

Figure 3B:
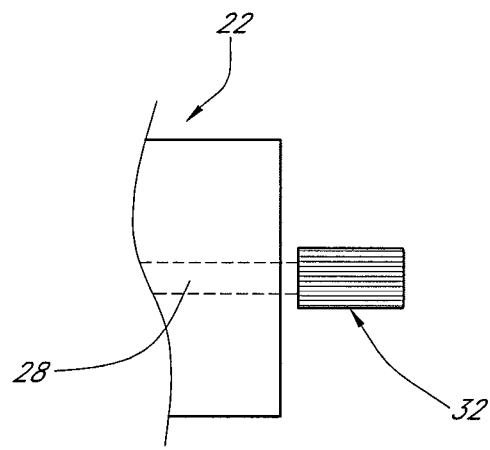
FIG. 3B is a detailed side view of a portion of the handle of the tunneling device of FIG. 1A.

Preferably, a connection fitting (e.g., a luer fitting 32) is positioned at the proximal end of the tunneling device 20 for facilitating the introduction of a fluid through the lumen 26 of the shaft 24. In FIGS. 1A and 3B, the connection fitting is a standard luer fitting 32 and is positioned at the proximal end of the handle 22 of the tunneling device 20. In order to convey fluid through the one or more lumens 26 to the openings 30 of the shaft 24, the user connects the fluid source (e.g., syringe, drug delivery pump, other device, etc.) to the luer fitting 32 and administers the fluid using any suitable method (e.g., actuating the syringe, activating an electric pump, operating a hand pump device, etc.). The user can preferably able to control when and how much fluid is administered through the tunneling device 20, taking into consideration the anticipated level of discomfort, dosage and other factors. The user may also change the fluid source during or after delivery of the tunneling device. Thus, the lumen 26 of the shaft 24 may include a check valve or another suitable flow control device to prevent blood or other bodily fluid from unintentionally flowing proximally through the lumen 26.

Typically, after the tunneling device 20 is advanced to a target location within the anatomy, the tunneling device 20 is removed for the subsequent delivery of one or more catheters, instruments or other item. In one embodiment, a catheter is delivered through the passageway created by the tunneling device 20. Alternatively, the catheter or other item may be delivered through a sheath 40 which was delivered simultaneously with the tunneling device 20 into the anatomy as described above. In such arrangements, the sheath 40 may be subsequently retracted from the anatomy while leaving the catheter or other item in place within the anatomy. Preferably, as discussed above and illustrated in FIG. 2B, the sheath 40 includes one or more seams 50 that facilitate removal of the sheath 40 after it has been withdrawn from the anatomy.

In addition, the tunneling device 20 may be used to facilitate other medical treatment functions. For example, the user may deliver an antibiotic or other medication within the anatomy through the one or more lumen 26 positioned within the shaft 24. Alternatively, the user may withdraw a fluid from the anatomy by introducing a vacuum through the lumen 26. This is especially useful for draining an undesirable fluid from an organ, cyst or other part of the anatomy. In other embodiments, the lumen 26 may be used to withdraw a tissue sample (e.g., biopsy) or other item or substance from the anatomy.

As discussed above with reference to the embodiments illustrated in FIGS. 5 and 6, the tunneling device may include a malleable shaft that can be shaped before and/or during delivery. Alternatively, a more rigid, pre-formed shaft can be preferably used that will retain its shape during the tunneling procedure. Depending on the particular procedure for which the tunneling is used, the depth and location of the targeted anatomical site, the malleability and other material properties of the shaft, the length of the tunneling device and other factors, the user may optionally shape the shaft during the tunneling procedure. Preferably, a user shapes the tunneling device by exerting a bending force directly on the shaft. In other embodiments, a tool or other device may be used to shape the shaft. The lumen and other openings within the shaft are configured to retain their integrity during the shaping of the tunneling device. Thus, the ability to direct one or more fluids through the shaft preferably is maintained at all times.

As illustrated in FIG. 2A, the tunneling device 20 may include a sheath 40 that is slidably positioned on the outside of the shaft 24. A tunneling device 20 with an outer sheath 40 may be delivered into the human anatomy as described above. Once delivered to the desired anatomical site, the tunneling device 20 can be withdrawn, leaving the sheath within the anatomy. In FIG. 2A, the sheath 40 includes a handle portion 42 that can be manipulated to maintain the sheath 40 within the anatomy as the tunneling device 20 is withdrawn. Preferably, the sheath 40 is configured to maintain its structural integrity after the shaft 24 has been retracted. After the shaft 24 has been retracted, the sheath 40 can be used as a conduit to introduce a fluid (e.g., medication), a medical device, a catheter or other item sized to fit within the sheath 40. The inner wall of the sheath 40 is preferably smooth to facilitate the delivery of another object.

The sheath 40 can be removed by directly retracting it from the anatomy. However, depending on what has been placed within the sheath 40 after removal of the tunneling device 20, it may not be easy, or even possible, to directly pull the sheath 40 out of the body. For example, a catheter or another medical device may have has been inserted within the sheath 40, and it is desirable to maintain such item with the anatomy while removing the sheath 40. Consequently, the sheath 40 can be configured with one or more longitudinal seams 50 (FIG. 2B) that permit the sheath 40 to be split into two or more pieces. In FIG. 2B, the sheath 40 includes two longitudinal seams, positioned opposite of one another. By separating the tabs 44 of the handle portion 42, the sheath 40 splits into two pieces, making it easier to remove the sheath 40 from a catheter or other object situated within the sheath 40. Typically, a catheter includes a luer fitting or similar feature near its proximal end that prevents an outer sheath 40 to be slidably separated from the catheter. Thus, the sheath 40 is advantageously configured with one or more seams so that it may be split into separate sections as it is being withdrawn or after it has been withdrawn. As illustrated in FIGS. 5 and 6, a sheath 40 may be optionally used on a tunneling device with a malleable shaft.

The tunneling device may be manufactured to be disposable or reusable. The tunneling device may be alternatively arranged so that only a portion of the device is reusable. For example, in one embodiment, the handle of the tunneling device may be reused while the shaft and other components, especially those that contact the anatomy and/or bodily fluids, are discarded after a single use.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A tunneling device for creating a subcutaneous path for placement of a catheter in a patient, comprising:
    an elongated shaft, said shaft having a body and a rounded distal end, said body comprising substantially the same diameter along its length up to the rounded distal end, said rounded distal end comprising a tapering cross-section along its length;
    at least one interior lumen extending along at least a portion of the elongated shaft, the at least one interior lumen having a closed distal end that ends prior to the distal end of said shaft;
    at least one outlet positioned on the body of the elongated shaft proximal to the tapering cross-section of the rounded distal end, said outlet extending from the at least one interior lumen to an external surface of said shaft for selectively delivering fluids therethrough, the at least one interior lumen extending distally past the at least one outlet to the closed distal end;
    a handle having a proximal end and distal end, said distal end of said handle configured with said shaft so as to permit a user of said tunneling device to grasp and manually manipulate said tunneling device;
    a sheath positioned over a portion of said shaft, said sheath comprising a handle portion at a proximal end thereof, said handle portion comprising two tabs opposite one another, each tab comprising two opposing raised contact members and a distal-side protrusion, wherein the distal-side protrusion extends from a distal edge of each tab, wherein one of the raised contact members is on a distal side of the handle portion and one of the raised contact members is on a proximal side of the handle portion such that the two opposing raised contact members are longitudinally aligned with each other on opposite sides of the tab, wherein the distal-side raised contact members of each tab restrict movement of the sheath relative to an adjacent object, and wherein the proximal-side raised contact members of each tab restrict movement of the sheath relative to said handle such that said sheath and said shaft can be advanced together within a body of a patient and wherein the handle portion and sheath are splittable when the two tabs are pulled apart; and
    a connection fitting positioned at a proximal end of the handle, wherein said connection fitting is configured to place the at least one interior lumen and the at least one outlet in fluid communication with a fluid source,
    wherein the elongated shaft comprises a rigidity sufficient to advance the tunneling device to a target location within the body of the patient.

2. The tunneling device of claim 1, wherein said shaft is malleable so as to permit a shape of said shaft to be altered prior to use of said tunneling device.

3. The tunneling device of claim 1, wherein said shaft has a non-linear shape.

4. The tunneling device of claim 3, wherein said shaft has a curved shape.

5. The tunneling device of claim 1, further including two outlets wherein the outlets are located approximately 180 degrees from one another.

6. A tunneling device for creating a path for placement of a catheter in a patient, comprising:
    an elongated shaft, said shaft having a body and a rounded distal end, said body comprising substantially the same diameter along its length up to the rounded distal end, said rounded distal end comprising a tapering cross-section along its length, said elongated shaft defining at least one interior lumen, the at least one interior lumen having a closed distal end that ends prior to the distal end of said shaft;
    a handle having a proximal end and distal end, said distal end of said handle configured with said shaft so as to permit a user of said tunneling device to grasp and manually manipulate said tunneling device;
    at least one fluid exit opening positioned on the body of said elongated shaft proximal to the tapering cross-section of the rounded distal end and extending from said at least one interior lumen to an external surface of said shaft for delivering fluids therethrough, the at least one interior lumen extending distally past the at least one outlet to the closed distal end;
    an inlet to said interior lumen to permit liquid to be introduced into said interior lumen and administered to the patient through said at least one fluid exit opening; and
    a sheath slidably positioned on said shaft, said sheath comprising a handle portion at a proximal end thereof, said handle portion comprising two tabs opposite one another, each tab comprising two opposing raised contact members and a distal-side protrusion, wherein the distal-side protrusion extends from a distal edge of each tab, wherein one of the raised contact members is on a distal side of the handle portion and one of the raised contact members is on a proximal side of the handle portion such that the two opposing raised contact members are longitudinally aligned with each other on opposite sides of the tab, wherein the distal-side raised contact members of each tab restrict movement of the sheath relative to an adjacent object, and wherein the proximal side raised contact members of each tab restrict movement of the sheath relative to said handle such that said sheath and said shaft can be advanced together within a body of a patient and wherein the handle portion and sheath are splittable when the two tabs are pulled apart,
    wherein the elongated shaft is generally rigid to help advance said tunneling device through anatomical tissue to a target location within the body of the patient.

7. The device of claim 6, further comprising a retractable needle located at said distal end of said shaft.

8. The device of claim 6, wherein said sheath is configured to longitudinally split into at least two portions.

9. The device of claim 6, wherein said inlet is located near a proximal end of said handle, further comprising a connector secured to the handle, said connector configured to permit said device to be connected to a fluid delivery device for delivery of a fluid to said lumen.

10. The device of claim 6, wherein said shaft is malleable to allow a shape of said shaft to be altered prior to use of said device.

11. The tunneling device of claim 6, further including two fluid exit openings wherein the fluid exit openings are located approximately 180 degrees from one another.

12. A tunneling device for creating a path for placement of a catheter in a patient, comprising:
- an elongated shaft, said shaft being substantially rigid and having a body and a rounded distal end, said body comprising substantially the same diameter along its length up to the rounded distal end, said rounded distal end comprising a tapering cross-section along its length;
- at least one interior lumen extending along at least a portion of the elongated shaft, the at least one interior lumen having a closed distal end that ends prior to the distal end of said shaft;
- at least one outlet positioned on the body of the elongated shaft proximal to the tapering cross-section of the rounded distal end, said outlet extending from the at least one interior lumen to an external surface of said shaft for selectively delivering fluids therethrough, the at least one interior lumen extending distally past the at least one outlet to the closed distal end;
- a handle having a proximal end and distal end, said distal end of said handle configured with said shaft so as to permit a user of said tunneling device to grasp and manually manipulate said tunneling device;
- a connection fitting positioned at a proximal end of the handle, wherein said connection fitting is configured to place the at least one interior lumen and the at least one outlet in fluid communication with a fluid source;
- wherein said shaft is malleable so as to permit a shape of said shaft to be altered prior to use of said tunneling device; and
- a sheath positioned over a portion of an outer surface of said shaft, said sheath comprising a handle portion at a proximal end thereof, said handle portion comprising two tabs opposite one another, each tab comprising two opposing raised contact members and a distal-side protrusion, wherein the distal-side protrusion extends from a distal edge of each tab, wherein one of the raised contact members is on a distal side of the handle portion and one of the raised contact members is on a proximal side of the handle portion such that the two opposing raised contact members are longitudinally aligned with each other on opposite sides of the tab, wherein the distal-side raised contact members of each tab restrict movement of the sheath relative to an adjacent object, and wherein the proximal-side raised contact members of each tab restrict movement of the sheath relative to said handle such that said sheath and said shaft can be advanced together within a body of a patient and wherein the handle portion and sheath are splittable when the two tabs are pulled apart,
- wherein the elongated shaft is configured to be selectively advanced through anatomical tissue to a target location within the patient.

13. The tunneling device of claim 12, wherein a cross-sectional shape of said handle is generally rectangular.

14. The tunneling device of claim 12, further comprising a retractable needle located at said distal end of said shaft.

15. The tunneling device of claim 12, wherein the connection fitting comprises a standard luer fitting.

16. The tunneling device of claim 15, wherein the luer fitting is adapted to receive a standard syringe.

17. The tunneling device of claim 1, wherein the connection fitting comprises a standard luer fitting.

18. The tunneling device of claim 12, further including two outlets wherein the outlets are located approximately 180 degrees from one another.

* * * * *